(12) United States Patent  
Johnson

(10) Patent No.: US 10,303,853 B2  
(45) Date of Patent: May 28, 2019

(54) SYSTEM AND METHOD FOR DATA ACCESS IN THE DISTRIBUTION OF LIMITED DISTRIBUTION DRUGS

(71) Applicant: IMS Health Incorporated, Danbury, CT (US)

(72) Inventor: Kjel Johnson, Winter Springs, FL (US)

(73) Assignee: IQVIA Inc., Parsippany, NJ (US)

(*) Notice: Subject to any disclaimer, the term of this patent is extended or adjusted under 35 U.S.C. 154(b) by 881 days.

(21) Appl. No.: 14/261,856

(22) Filed: Apr. 25, 2014

(65) Prior Publication Data

US 2015/0199492 A1    Jul. 16, 2015

Related U.S. Application Data

(60) Provisional application No. 61/925,937, filed on Jan. 10, 2014.

(51) Int. Cl.
| | |
|---|---|
| *G16H 20/00* | (2018.01) |
| *G06F 19/00* | (2018.01) |
| *G16H 20/10* | (2018.01) |

(52) U.S. Cl.
CPC .......... *G06F 19/3456* (2013.01); *G06F 19/00* (2013.01); *G16H 20/10* (2018.01)

(58) Field of Classification Search
CPC ........ G06Q 50/22; G06Q 50/24; G06F 19/30; G06F 19/3456; G06F 19/3462; G06F 19/326; G06F 19/328; G16H 10/00; G16H 10/20; G16H 10/40; G16H 10/60; G16H 10/65; G16H 15/00; G16H 20/00; G16H 20/10; G16H 20/13; G16H 20/17;

(Continued)

(56) References Cited

U.S. PATENT DOCUMENTS 6,315,720 B1 * 11/2001 Williams .............. G06F 19/322  
235/375  
7,765,110 B1 * 7/2010 Koneru ............... G06F 19/3456  
705/2

(Continued)

OTHER PUBLICATIONS

"Understanding Prescription Assistance Programs (PAPs)", www.talkaboutrx.org/paps.jsp, Jul. 18, 2013.*

(Continued)

*Primary Examiner* — Joseph D Burgess  
(74) *Attorney, Agent, or Firm* — Fish & Richardson P.C.

(57) ABSTRACT

A computer-assisted method that includes: receiving a first list of data entries set forth by a first pharmaceutical manufacturer for a first limited distribution drug for a target condition; receiving first prescription data from a server at a first specialty pharmacy authorized to distribute the first limited distribution drug, the first prescription data initiated by a patient, at the first specialty pharmacy, for whom a healthcare provider of the patient had prescribed the limited distribution drug; automatically generating first report data entries based on the first prescription data and according to the first list set forth by the first pharmaceutical manufacturer, the first report data entries devoid of information identifying the patient or the prescribing healthcare provider; transmitting the generated first report data entries to the first pharmaceutical manufacturer; and receiving a response from the first pharmaceutical manufacturer.

17 Claims, 3 Drawing Sheets

(58) Field of Classification Search
CPC ........ G16H 20/30; G16H 20/40; G16H 20/60;
G16H 20/70; G16H 20/90; G16H 30/00;
G16H 40/00; G16H 40/20; G16H 40/40;
G16H 40/60; G16H 40/63; G16H 40/67;
G16H 50/00; G16H 70/00; G16H 70/20;
G16H 70/40; G16H 70/60; G16H 80/00
See application file for complete search history.

(56) References Cited

U.S. PATENT DOCUMENTS

| | | | | |
|---|---|---|---|---|
| 8,306,829 B2* | 11/2012 | Starkey | ................ | G06F 19/322 |
| | | | | 705/2 |
| 2003/0050825 A1* | 3/2003 | Gallivan | ................ | G06Q 30/02 |
| | | | | 705/14.52 |
| 2003/0093295 A1* | 5/2003 | Lilly | ................... | G06F 19/3456 |
| | | | | 705/2 |
| 2009/0216560 A1* | 8/2009 | Siegel | ................ | G06F 19/3456 |
| | | | | 705/3 |
| 2011/0191245 A1* | 8/2011 | Ricciardi | ............... | G06Q 10/10 |
| | | | | 705/51 |
| 2011/0282690 A1* | 11/2011 | Patel | ................. | G06Q 30/0603 |
| | | | | 705/3 |
| 2014/0136237 A1* | 5/2014 | Anderson | ............. | G06F 19/328 |
| | | | | 705/3 |
| 2014/0249832 A1* | 9/2014 | Link | ..................... | G06Q 50/22 |
| | | | | 705/2 |

OTHER PUBLICATIONS

"Program Design Snapshot: Paperless Income Verification", Georgetown University Health Policy Institute, Center for Children and Families, Mar. 2009.*

* cited by examiner

SYSTEM AND METHOD FOR DATA ACCESS IN THE DISTRIBUTION OF LIMITED DISTRIBUTION DRUGS

CROSS REFERENCE TO RELATED APPLICATIONS

This application claims benefit of U.S. provisional Patent Application 61/925,937, filed Jan. 10, 2014, the entire contents of which are incorporated by reference in their entirety for all purposes.

BACKGROUND

The advent of the Internet and mobile applications ("apps") has provided new venue for sharing information between healthcare product manufacturers, distributors, and insurance payors.

OVERVIEW

In one aspect, some implementations provide a computer-implemented method including: receiving a first list of data entries set forth by a first pharmaceutical manufacturer for a first limited distribution drug for a target condition, the first list of data entries provided by a server at the first pharmaceutical manufacturer of the first limited distribution drug; receiving first prescription data from a server at a first specialty pharmacy authorized to distribute the first limited distribution drug, the first prescription data initiated by a patient, at the first specialty pharmacy, for whom a healthcare provider of the patient had prescribed the limited distribution drug; automatically generating first report data entries based on the first prescription data and according to the first list set forth by the first pharmaceutical manufacturer, the first report data entries devoid of information identifying the patient or the prescribing healthcare provider; transmitting the generated first report data entries to the first pharmaceutical manufacturer; and receiving a response from the first pharmaceutical manufacturer.

Implementations may include one or more of the following features. Some implementations may further include: receiving second prescription data from a server at a second specialty pharmacy authorized to distribute the first limited distribution drug, the second prescription data also initiated by the patient, at the second specialty pharmacy, for whom the healthcare provider of the patient had prescribed the first limited distribution drug, the second specialty pharmacy different from the first specialty pharmacy; and automatically generating second report data entries based on the prescription data and according to the list set forth by the pharmaceutical manufacturer, the second report data entries devoid of information identifying the patient or the prescribing healthcare provider. The implementations may additionally include: transmitting the generated second report data entries to the pharmaceutical manufacturer, the second report data entries linked to the first report data entries.

In the implementations, receiving the first prescription data from the server at the first specialty pharmacy may further include receiving the first prescription data from the server at the first specialty pharmacy authorized by a first healthcare insurance carrier, and wherein receiving the second prescription data from the server at the second specialty pharmacy comprises receiving the second prescription data from the server at the second specialty pharmacy authorized by a second healthcare insurance carrier, different from the first healthcare insurance carrier.

Some implementations may include: receiving a second list of data entries set forth by a second pharmaceutical manufacturer for a second limited distribution drug for the same target condition, the second list of data entries provided by a server at the second pharmaceutical manufacturer of the limited distribution drug. The implementations may additionally include: receiving second prescription data from the server at the first specialty pharmacy authorized to distribute the second limited distribution drug for the same target condition, the second prescription data originally initiated by the patient, at the first specialty pharmacy, for whom the healthcare provider of the patient had prescribed the second limited distribution drug to replace the first limited distribution drug; and generating second report data entries based on the second prescription data and according to the second list set forth by the second pharmaceutical manufacturer, the second report data entries devoid of information identifying the patient or the prescribing healthcare provider. The implementations may further include: transmitting the generated second report data entries to the second pharmaceutical manufacturer, the second report data entries linked to the first report data entries. In the implementations, receiving the second list of data entries set forth by the second pharmaceutical manufacturer may include: receiving the second list of data entries set forth by the second pharmaceutical manufacturer different from the first pharmaceutical manufacturer. In the implementations, receiving the second list of data entries set forth by the second pharmaceutical manufacturer may include: receiving the second list of data entries set forth by the second pharmaceutical manufacturer identical to the first pharmaceutical manufacturer.

In some implementations, receiving the first prescription data may include receiving a request originally from the patient to participate in a patient-assistance-program (PAP) offered by the first pharmaceutical manufacturer. In the implementations, generating first report data entries may include generating a participation request to participate in the PAP offered by the first pharmaceutical manufacturer, the participation request comprising income characteristics of the patient but devoid of information identifying the patient or the prescribing healthcare provider. In the implementations, transmitting the generated first report data entries comprises: transmitting the generated first report data entries that includes the participation request. In the implementations, receiving the response from the first pharmaceutical manufacturer may include: receiving a determination result from the first pharmaceutical manufacturer of whether the patient is allowed to participate in the PAP. The implementations may further include, in response to receiving a determination result that the patient is allowed to participate in the PAP, updating a healthcare insurance carrier of the patient of the determination result.

In the implementations, generating the participation request may further include querying a government agency to confirm the income characteristics of the patient. In the implementations, transmitting the generated first report data entries may include: transmitting the generated first report data entries that includes the participation request with the income characteristics of the patient confirmed.

Some implementations may include: forwarding at least a portion of the first report data entries to a regulatory agency. In the implementations, forwarding at least a portion of the first report data entries comprises forwarding at least a portion of the first report data entries to comply with a risk mitigation strategy in consuming the first limited distribution drug.

DETAILED DESCRIPTION

This disclosure generally describes a system and method for providing improved data access to pharmaceutical manufacturers regarding the prescription of limited distribution drugs (LDDs) at specialty pharmacies. The improved data access may provide pharmaceutical manufacturers with more accurate monitoring information while reducing administrative overheads. Specialty pharmacies may see improved operation efficiency stemming from less data entry and fewer calls to doctor's offices. The improved data access may also mitigate hassles to healthcare providers (for example, prescribing physicians) in interacting with specialty pharmacies. Due to reduced hassle, healthcare providers may prescribe drugs to patients based on merits, rather than on convenience or expediency. Last, but not least importantly, the improved data access may help patients to receive limited distribution drugs (LDDs) faster. Through the improved data access, the patient may also experience higher likelihood to qualify for patient-assistance-programs (PAPs) offered by a particular pharmaceutical manufacturer.

When a patient receives a prescription of a limited distribution drug from a treating physician, the prescription may be filled at a specialty pharmacy. Limited Distribution Drugs (LDD) may include medications that are distributed to either one or a very limited number of pharmacies and wholesalers. This group of drugs is usually used to treat conditions that only affect a small patient population and may have special and complex dosing requirements that need to be continually monitored or might be required by the Food and Drug Administration (FDA) for drug approval. For example, limited distribution drugs may include drugs with complex oral dosing or intra-venous (IV) injection dosing requirements. Through limited distribution at specialty pharmacies, LDD pharmaceutical manufacturers can ensure that those who distribute the medication have adequate training on the necessary monitoring to reduce risk and help the pharmaceutical manufacturer track inventory.

Figure 1:
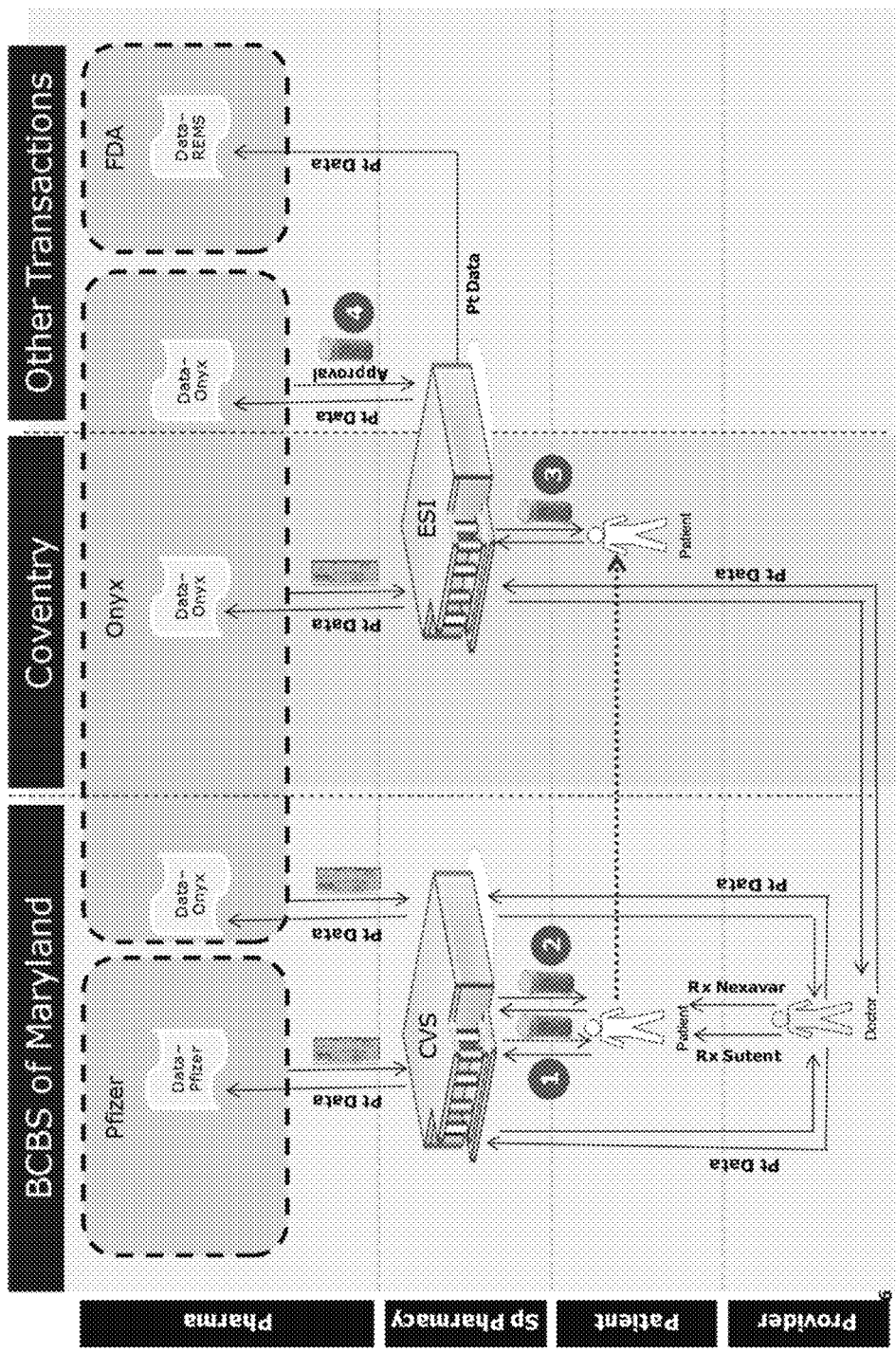
FIG. 1 is a diagram illustrating existing work flow to provide patients access to limited distribution drugs.

FIG. 1 is a diagram illustrating current work flow to provide patients access to limited distribution drugs. The illustration is for a target condition of renal cell carcinoma (RCC). In the illustration, patient may initially carry blue cross blue shield (BCBS) of Maryland designating specialty pharmacy of CVS as the exclusive specialty pharmacy for RCC drugs. Here, the RCC drugs treat renal carcinoma only and generally include expensive cocktails for chemotherapy. As of this disclosure, approximately seven LDDs are on the market for treating RCC. These RCC drugs are typically oral chemotherapies. In the illustration, the patient may be initially prescribed with Sutent for treating kidney cancer.

The patient may approach specialty pharmacy CVS to fill the prescription, as illustrated by arrow 1. Because Sutent is an LDD, specialty pharmacy CVS may confirm the prescription status with the prescribing doctor, to comply with, for example, relevant regulations on distribution of LDDs. The confirmation generally means that specialty pharmacy CVS may call up the prescribing doctor's office to verify the prescription, including the dosing amount and duration.

When the prescribing doctor has confirmed the prescription, specialty pharmacy CVS may then engage the pharmaceutical manufacturer, in this case, Pfizer. In particular, the specialty pharmacy CVS may submit prescription data to Pfizer to report the distribution of the prescribed dose. Generally, the reporting data is de-identified to comply with, for example HIPPA (Health Insurance Portability and Accountability Act) regulations to protect the privacy and confidentially of the patient. Once the reporting data has been successfully submitted, Pfizer may approve the distribution and log the distribution to comply with regulations. Often times, Pfizer, as a pharmaceutical manufacturer may reimburse a nominal sum to specialty pharmacy CVS for submitting the prescription data. Specialty pharmacy CVS may then proceed with distributing the prescribed dose of Sutent to the patient, as indicated by arrow 2.

Thereafter, the patient may not show any signs of response to the chemotherapy as administered through the dosing of Sutent. In one example situation, the patient may see the treating doctor in a follow-up visit. The treating doctor may then prescribe Nexaver, another kidney cancer treatment. The patient may approach specialty pharmacy CVS and repeat the above process, as indicated by arrow 3.

One difference, though, is that the pharmaceutical manufacturer is now Onyx, a different manufacturer. Each pharmaceutical manufacturer may have a corresponding list of data entries that the manufacturer may require from specialty pharmacies to report prescription data. Here, Onyx may have a different list of data entries from Pfizer. Hence, specialty pharmacy CVS may generate the reporting data entries anew.

The duplication is not limited to reporting data entries. Because Nexaver is also an LDD, specialty pharmacy CVS may confirm with treating doctor again to comply with regulations on distributing LDDs. Sometimes, the hassle of duplicated confirmation can hinder treatment adjustments prescribed by treating doctors.

More interestingly, when the patient switches insurance carrier, the duplication can propagate more. As disclosed herein, a healthcare insurance carrier may include any private insurance companies, for example, blue cross blue shield, MetLife, Delta, etc. The healthcare insurance carrier may also include any government-run healthcare programs, including Medicare, Medicaid, Medi-Cal, etc. In the illustration, the patient switches from BCBS of Maryland to Coventry, as a new healthcare insurance carrier. Specialty pharmacy ESI may be the sole distributor of LDD for Coventry in the state of Maryland. The patient now approaches specialty pharmacy to fill the prescription for Nexaver. The duplication is abundant.

First, specialty pharmacy ESI communicates with the treating doctor, typically, the treating doctor's office staff, to confirm the prescription status. The confirmation may be mandated by regulations on distributors of LDDs. As noted above, the hassle factor presented to the treating doctor's staff may hinder the distribution of Nexaver to the patient.

After receiving confirmation from the treating doctor, specialty pharmacy ESI may then engage the pharmaceutical manufacturer, in this case, Onyx. As Onyx may have its own desired list of data entries, specialty pharmacy ESI may generated reporting data entries accordingly. Most times, the data entries are duplicate data entries as would be reported to Pfizer. For example, in some cases, thirty five out of forty reported data entries are the same data entries reported to other pharmaceutical manufacturers. Yet, the sequencing order and reporting format would be dependent on the particular pharmaceutical manufacturer. Additionally, some data entries may be unique to a particular LDD, for example, a side-effect, etc. The following list shows the example data entries set forth for a LDD.

SP patient ID# (encrypted)
Gender
DOB or year of birth
Primary Insurance ID#
Insurance Name
Insurance Type
Commercial
Medicare
Medicaid
Cash
Insurance Phone #
BIN # (PBM)
PCN # (PBM)
Duplicate all insurance info above for Secondary Insurance
Physician 1$^{st}$ name
Physician last name
NPI
State License
City/state/zip
Shipment Information:
SPP name (ID code provided)
Ship date
Quantity shipped
NDC
Drug name
Fill
  New rx
  Or refill
Copay type?
Copay or coinsurance
ICD9
Prior lines of therapy
Prescription Record Type:
Referral
Current status
Dispense type
Transfer
Benefits Investigation only
Prescription Order Number
Refill (1$^{st}$, 2$^{nd}$, 3$^{rd}$)
Or N (for new rx)
Referral Date Received
Referral completion date
Referral status
Reason:
Not approved for diagnosis
Pt denied
Physician cancelled
Lab values
Serum Ferritin levels After the reporting data entries have been successfully submitted at Onyx, the pharmaceutical manufacturer Onyx may compensate specialty pharmacy ESI with a nominal fee, even though, the same list of reporting data entries may be received from specialty pharmacy CVS before the patient switched healthcare insurance carrier.

LDD tends to be expensive drugs. For example, some LDDs can run at a rate of 20 k-25 k per month. The patient may soon face dire economic straits after consuming an LDD. Fortunately, most pharmaceutical manufacturers administer some form of a patient-assistance-program (PAP) to ease the economic burden on patients. PAP may also be known as prescription assistance program. The overarching theme is that most pharmaceutical manufacturers are willing to help out patients based on financial need, as determined by income levels (for example, based on portions of income subject to social security tax). The PAP may be more prevalent for certain target conditions, such as cancer, human immunodeficiency virus (HIV), etc.

Nonetheless, when a patient submits a request to participate in a PAP of a particular pharmaceutical manufacturer, more overhead may be incurred. In the example illustrated by FIG. 1, the specialty pharmacy ESI may first confirm the prescription status with the prescribing doctor. The same hassle of duplicative communication is imposed on the prescribing doctor, which may hinder the distribution of Nexaver to the patient.

When the prescribing doctor confirms the prescription status for Nexaver, specialty pharmacy ESI may generate reporting data entries according to a required list of data entries set forth by Onyx. The reporting data entries may include a particular request to participate in the PAP of Onyx.

When the reporting data entries have been successfully submitted at Onyx, the pharmaceutical manufacturer may compensate specialty pharmacy ESI for submitting the data entries. The pharmaceutical manufacturer may further verify the income level of the patent requesting participation. Due to HIPPA implementations, the data entries submitted to a pharmaceutical manufacturer, as well as the request to participate in a PAP, are generally devoid of information identifying the patient. The pharmaceutical manufacturer may have rather limited means for the verification. Hence, the pharmaceutical manufacturer may rely on the authenticity or veracity of the submitted request itself and may impose strict restrictions on the type of patients who may participate in a PAP through a specialty pharmacy. The restrictive nature may operate counter-productively to disqualify many patients who would otherwise qualify based on their income.

As illustrated in FIG. 1, under Risk Evaluation and Mitigation Strategy (REMS) initiative, specialty ESI may be obligated to regularly report prescription data to regulating agencies such as the Federal Drug Administration (FDA). The reporting obligations may pose added overhead to specialty pharmacy ESI. The added burden may represent increase reporting hassle.

In sum, the as-is work flow is fraught with peril. Each pharmaceutical manufacturer may require different formats of data entries. None pharmaceutical manufacturer may be able to correlate a present data entry to an earlier one from the same patient, because each pharmaceutical manufacturer may only see de-identified data entries that are devoid of information identifying the patient or the prescribing healthcare provider (including treating physicians, doctors, etc.). Each healthcare insurance carrier may have a sole specialty pharmacy for distributing a limited distribution drug manufactured by a particular pharmaceutical manufacturer. Generally, a sole distributor arrangement means that a pharmaceutical manufacturer and a specialty pharmacy deal with each other as determined by the healthcare insurance carrier of the patient, any pre-existing agreement between a pharmaceutical manufacturer and a specialty pharmacy may not be based on a pre-existing agreement that could have set forth the communication protocols between the two. The lack of a communication protocol generally renders the pharmaceutical manufacturer unable to resolve data entries initially from the same patient for the same limited distribution drug. As a result, the pharmaceutical manufacturer may not accurately track the dosing of a particular patient on a given limited distribution drug. Likewise, the pharmaceutical manufacturer may not know the treatment history of the particular patient to better understand drug interactions of the particular patient. Yet, the pharmaceutical manufacturer simply compensates the specialty pharmacy for all data entries, regardless of the abundant duplications. What's more, the process tends to be manual, and prone to human errors (from fatigue or erroneous perception). The dreaded process may amplify the inherent hassles to the disadvantage of patients. In the end, to get the information from the prescribing doctor; collect the information from the patient; send the data entries to the pharmaceutical manufacturer; and distribute the limited distribution drug to the patient— the whole process, from when the prescription arrives at a specialty pharmacy to when the patient gets the prescribed limited distribution drug prescription, may take 7 to 14 days in the current work flow.

Nonetheless, limited distribution drug may not be overlooked. At the time of this disclosure, approximately 120 limited distribution drugs (LDDs) are on the market. More than 50% of these LDDs relate to oral chemotherapy treatments. About one in seven of the drugs in the pipe line are LDDs. Although the projected sales for blockbuster drugs may be flat in the foreseeable future, the market size for LDDs may amount to $10.6 billion in 2013 and may grow at about 15% year to year.

The administrative expense for the pharmaceutical manufacturers in dealing with reported data entries of limited distribution drugs is estimated to be about $100 million. These expenses are associated with a dreaded administrative process for patients, healthcare providers, and specialty pharmacies, as discussed above. The proposed workflow herein may serve a middle man function to automatically interface specialty pharmacies to the pharmaceutical manufacturers. Some implementations may capture clinically valuable information to enable pharmaceutical manufacturers to obtain more accurate monitoring information on patients on a particular limited distribution drug (LDD).

Figure 2:
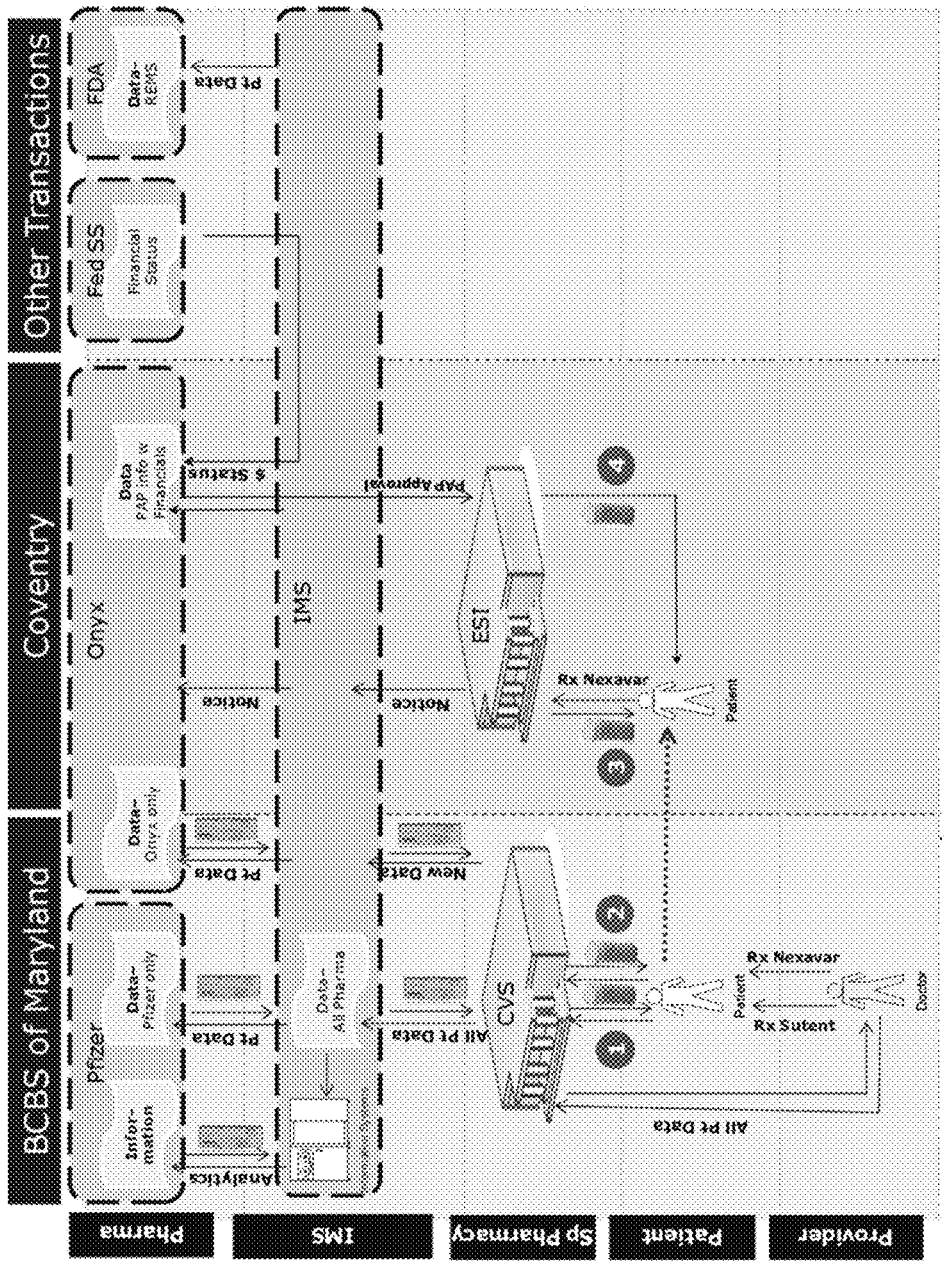
FIG. 2 is a diagram illustrating an example work flow to provide patients access to limited distribution drugs, according to some implementations.

FIG. 2 is a diagram illustrating proposed work flow to provide patients access to limited distribution drugs, according to some implementations. The illustration is for a target condition of renal cell carcinoma (RCC). The work flow for other types of conditions may follow the same inventive spirit as disclosed herein. In the illustration, patient may initially carry blue cross blue shield (BCBS) of Maryland designating specialty pharmacy of CVS as the exclusive specialty pharmacy for RCC drugs. In the illustration, the patient may be initially prescribed with Sutent for treating kidney cancer.

The patient may approach specialty pharmacy CVS to fill the prescription, as illustrated by arrow 1. The prescription may be entered into a computer at specialty pharmacy CVS for further processing in accordance with the disclosure herein. Because Sutent is an LDD, specialty pharmacy CVS may confirm the prescription status with the prescribing doctor, to comply with, for example, relevant regulations on distribution of LDDs. The confirmation generally means that specialty pharmacy CVS may call up the prescribing doctor's office to verify the prescription, including the dosing amount and duration. In this illustration, specialty pharmacy may only need to confirm the prescription once, the very first time.

When the prescribing doctor has confirmed the prescription, specialty pharmacy CVS may then engage a middle layer. The middle layer may be implemented as a data service between, for example, specialty pharmacies and treating healthcare providers. Noticing that the prescription LDD is a Pfizer drug, the middle layer may generate reporting data entries according to a template of data entries provided by Pfizer. The Pfizer template may be specific to Pfizer requirements, as provided by, for example, a server computer associated with Pfizer. Nonetheless, about 85% of data entries may be identical for all pharmaceutical manufacturers. These data entries may include, for example, age of patient, stage of tumor, etc. Other data entries may be more specific to each LDD, for example, specific side-effects, etc. Generating the reporting data entries may be a tedious process and prone to human errors. As such, generating the data entries can be more suitable for machine implementations when voluminous data entries are generated routinely, for example, at each participating specialty pharmacies and for each LDD prescription. Once reporting data entries are generated for Pfizer, the reporting data entries may be submitted to Pfizer. As noted above, the submitted reporting data entries are devoid of information identifying the patient or the prescribing doctor, in compliance with HIPPA (Health Insurance Portability and Accountability Act) regulations that protect the privacy and confidentially of the patient. Once the reporting data entries have been successfully submitted, Pfizer may approve the distribution and log the distribution to comply with regulations. The middle layer may relay the approval to the specialty pharmacy so that the specialty pharmacy CVS may then proceed with distributing the prescribed dose of Sutent to the patient, as illustrated by arrow 2.

Thereafter, the patient may not show any signs of response to the chemotherapy as administered through the dosing of Sutent. In one example situation, the patient may see the treating doctor in a follow-up visit. The treating doctor may then prescribe Nexaver, another kidney cancer treatment, to replace Sutent treatment. The patient may approach specialty pharmacy CVS to fill the prescription.

The pharmaceutical manufacturer of Nexaver is Onyx. As noted above, each pharmaceutical manufacturer may have a corresponding list of data entries that the manufacturer may require from specialty pharmacies to report prescription data. Here, Onyx may have a different list of data entries from Pfizer. In the illustration of FIG. 1, specialty pharmacy CVS would have to generate the reporting data entries anew. In comparison, specialty pharmacy CVS in FIG. 2 may rely on the middle layer to generate the new reporting data entries for Onyx. Because, Nexaver is a replacement treatment for an existing target condition on the same patient who used to be on Sutent, the middle layer may take note in generating the reporting data entries so that Onyx could know that the subject was treated with Sutent. The information of previous drug treatment may provide valuable information to reveal, for example, drug interactions in this context. Specifically, after submitting the reporting data entries to Onyx, according to a template of Onyx data entries, Onyx may respond with an approval notice. The middle layer may relay the approval notice to the specialty pharmacy so that specialty pharmacy CVS may proceed with distributing Nexaver.

Another distinction from the illustration in FIG. 1 is that specialty pharmacy CVS may not need to call up the treating healthcare provider's office to verify the prescription as authentic and genuine. As noted above, the middle layer kept a record of the confirmation when the patient approached CVS pharmacy with the Sutent prescription in the first instance. Hence, additional overhead time may be saved. Access to the middle layer may be extended to payors such that prior authorization/utilization management endeavors could be accomplished electronically, rather than by a call to the treating healthcare provider's office.

Thereafter, the patient may switch healthcare insurance carrier, from BCBS of Maryland to Coventry. Specialty pharmacy ESI may be the sole distributor of LDD for Coventry in the state of Maryland. The patient now approaches specialty pharmacy to fill the prescription for Nexaver, as illustrated by arrow 3. The abundant duplications in FIG. 1 may be reduced substantially and the specialty pharmacy may proceed with dispensing the prescribed LDD more efficiently, as shown by arrow 4.

First, specialty pharmacy ESI may communicate with the middle layer to determine that the patient has existing prescription at a different specialty pharmacy. As a result, specialty pharmacy ESI may not need to communicate with the treating doctor, typically, the treating doctor's office staff, to confirm the prescription status. The confirmation may be mandated by regulations on distributors of LDDs. In comparison to the illustration in FIG. 1, the hassle factor presented to the treating doctor's staff may be obviated.

Second, middle layer may generate reporting data entries in accordance with an existing template of data entries required by Onyx. As discussed above, in some implementations, the middle layer would relieve specialty pharmacies from the onerous burdens of coping with each and every pharmaceutical manufacturer. Notably, a specialty pharmacy may have a contract of distribution with a healthcare insurance carrier. The contract of distribution may be render a specialty pharmacy as an exclusive or sole distributor. However, the contract of distribution may not include an agreement or a communication protocol between the specialty pharmacy and a pharmaceutical manufacturer. As noted above, the absence can lead to many missed opportunities and increased overhead, both to the disadvantage of patients. In contrast, the reporting data entries, according to the disclosure herein, would enable pharmaceutical manufacturers to obtain more accurate monitoring information on a particular LDD and relieve specialty pharmacies of the onerous burden of coping with the reporting requirements from the pharmaceutical manufacturers. But the benefits may be more far-reaching.

Third, the patient may soon opt for a patient-assistance-program (PAP) offered by a pharmaceutical manufacturer in coping with the cost of the LDD. As illustrated, the patient may submit a request to participate in a PAP of a particular pharmaceutical manufacturer. In contrast to the illustration of FIG. 1, administrative overhead associated with processing the submitted PAP request may be substantially reduced.

With the middle layer to keep track of the LDD status of the patients, the specialty pharmacy may no longer need to call up the treating healthcare provider's office to verify the underlying prescription. In some instances, the middle layer may obtain data entries for an LDD from the electronic medical record at, for example, the treating physician's office. The middle layer may also populate reporting data entries to include a request to participate in the PAP program. In return, the pharmaceutical may request the middle layer to verifying an income status of the patient, for example, if the patient's taxable income has reached various thresholds as set forth in the PAP. In response, the middle layer may query a third-party entity to verify the income characteristics. For example, the middle layer may query the social security administration to obtain a binary answer (yes or no) regarding the social security tax the patient may have paid in the past tax year. The confirmation may be relayed to the pharmaceutical manufacturer for the pharmaceutical manufacturer to determine the patient's eligibility in a PAP. As noted above, Due to HIPPA implementations, the data entries submitted to a pharmaceutical manufacturer, as well as the request to participate in a PAP, are generally devoid of information identifying the patient. With the middle layer functioning as a conduit, no privacy or confidentiality may be compromised. Yet, the pharmaceutical manufacturer may have some means to verify the income level of a patient to determine the patient's eligibility in a PAP. Hence, patients who otherwise would be impractical to be determined for a PAP may now have their income characteristics verified so that they may be admitted to a PAP to reap the financial benefits.

As illustrated in FIG. 2, under Risk Evaluation and Mitigation Strategy (REMS) initiative, specialty ESI may be obligated to regularly report prescription data to regulating agencies such as the Federal Drug Administration (FDA). In contrast to the illustration in FIG. 1 where the reporting obligations may pose added overhead to specialty pharmacy ESI, here, in FIG. 2, with the middle layer fulfilling the middle function, specialty pharmacy ESI is relieved from such regulatory obligations. In other words, specialty pharmacy may rely on the middle layer to handle the reporting overhead. The middle layer may also be better positioned to report more accurate information, such as dosing information, in a Risk Evaluation and Mitigation Strategy (REMS) initiative. The REMS initiative may be one example of a risk evaluation protocol capable of being implemented in accordance with the disclosure herein.

Figure 3:
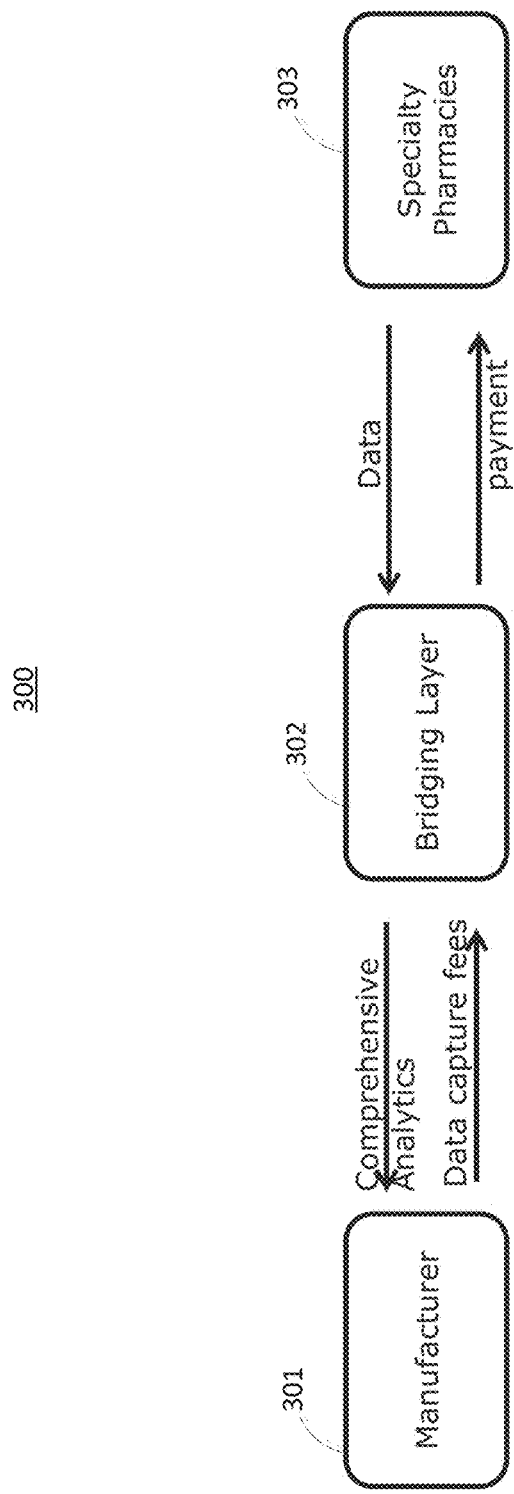
FIG. 3 is a diagram highlighting a bridging function to provide information access to prescription-based limited distribution drugs according to some implementations.

FIG. 3 is a diagram 300 highlighting a bridging function to provide access to limited distribution drugs according to some implementations. A middle layer 302 may facilitate the communication between the pharmaceutical manufacturers 301 and the specialty pharmacies 303. Middle layer 302 may represent an additional infrastructure to supplement the healthcare system to reduce, for example, administrative overhead, dispensing latency, etc. Middle layer 302 may include data servers, data storage devices, network interfaces, as well as data security and reliability mechanism as disclosed herein. A particular pharmaceutical manufacturer 301 may funnel payment to the middle layer 302 as data-capture fees. The middle layer 302 may pass portions of the payment to specialty pharmacies 303 in the distribution of LDDs manufactured by the pharmaceutical manufacturer 301. The passed on payment may compensate the specialty pharmacies 303 to make infrastructure improvements to use the technology offered by the middle layer 302. The data submitted by specialty pharmacies 303 to fill prescriptions presented by the patients may be processed and analyzed by the middle layer 302. For example, the middle layer 302 may include features to link reporting data entries from the same patient while reporting the linked the data entries to the pharmaceutical manufacturer 301. Access to data maintained at the middle layer 302 may be extended to healthcare insurance carriers—the payors. In some instances, middle layer 302 may receive information regarding a prescription for an LDD directly from a treating healthcare provider. As noted above, the manual work flow may lead to a latency of 7-14 days from the presentation of prescription by the patient to the delivery of the prescribed LDD. With the automated system disclosed herein, the latency may be substantially reduced. In some instances, the latency may be reduced from weeks to days or even hours.

Implementations of the subject matter and the functional operations described in this specification can be implemented in digital electronic circuitry, in tangibly-implemented computer software or firmware, in computer hardware, including the structures disclosed in this specification and their structural equivalents, or in combinations of one or more of them. Implementations of the subject matter described in this specification can be implemented as one or more computer programs, i.e., one or more modules of computer program instructions encoded on a tangible non-transitory program carrier for execution by, or to control the operation of, data processing apparatus. The computer storage medium can be a machine-readable storage device, a machine-readable storage substrate, a random or serial access memory device, or a combination of one or more of them.

The term "data processing apparatus" refers to data processing hardware and encompasses all kinds of apparatus, devices, and machines for processing data, including, by way of example, a programmable processor, a computer, or multiple processors or computers. The apparatus can also be or further include special purpose logic circuitry, e.g., a central processing unit (CPU), a FPGA (field programmable gate array), or an ASIC (application-specific integrated circuit). In some implementations, the data processing apparatus and/or special purpose logic circuitry may be hardware-based and/or software-based. The apparatus can optionally include code that creates an execution environment for computer programs, e.g., code that constitutes processor firmware, a protocol stack, a database management system, an operating system, or a combination of one or more of them. The present disclosure contemplates the use of data processing apparatuses with or without conventional operating systems, for example Linux, UNIX, Windows, Mac OS, Android, iOS or any other suitable conventional operating system.

A computer program, which may also be referred to or described as a program, software, a software application, a module, a software module, a script, or code, can be written in any form of programming language, including compiled or interpreted languages, or declarative or procedural languages, and it can be deployed in any form, including as a stand-alone program or as a module, component, subroutine, or other unit suitable for use in a computing environment. A computer program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a communication network. While portions of the programs illustrated in the various figures are shown as individual modules that implement the various features and functionality through various objects, methods, or other processes, the programs may instead include a number of sub-modules, third party services, components, libraries, and such, as appropriate. Conversely, the features and functionality of various components can be combined into single components as appropriate.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, e.g., a central processing unit (CPU), a FPGA (field programmable gate array), or an ASIC (application-specific integrated circuit).

Computers suitable for the execution of a computer program include, by way of example, can be based on general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer-readable media (transitory or non-transitory, as appropriate) suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The memory may store various objects or data, including caches, classes, frameworks, applications, backup data, jobs, web pages, web page templates, database tables, repositories storing business and/or dynamic information, and any other appropriate information including any parameters, variables, algorithms, instructions, rules, constraints, or references thereto. Additionally, the memory may include any other appropriate data, such as logs, policies, security or access data, reporting files, as well as others. The processor and the memory can be supplemented by, or incorporated in, special purpose logic circuitry.

To provide for interaction with a user, implementations of the subject matter described in this specification can be implemented on a computer having a display device, e.g., a CRT (cathode ray tube), LCD (liquid crystal display), or plasma monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

The term "graphical user interface," or GUI, may be used in the singular or the plural to describe one or more graphical user interfaces and each of the displays of a particular graphical user interface. Therefore, a GUI may represent any graphical user interface, including but not limited to, a web browser, a touch screen, or a command line interface (CLI) that processes information and efficiently presents the information results to the user. In general, a GUI may include a plurality of user interface (UI) elements, some or all associated with a web browser, such as interactive fields, pull-down lists, and buttons operable by the business suite user. These and other UI elements may be related to or represent the functions of the web browser.

Implementations of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network (LAN), a wide area network (WAN), e.g., the Internet, and a wireless local area network (WLAN).

The computing system can include clients and servers. A client and server are generally remote from each other and typically interact through a communication network. The relationship of client and server arises by virtue of computer programs running on the respective computers and having a client-server relationship to each other.

While this specification contains many specific implementation details, these should not be construed as limitations on the scope of any invention or on the scope of what may be claimed, but rather as descriptions of features that may be specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combinations.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be helpful. Moreover, the separation of various system modules and components in the implementations described above should not be understood as requiring such separation in all implementations, and it should be understood that the described program components and systems can generally be integrated together in a single software product or packaged into multiple software products.

Particular implementations of the subject matter have been described. Other implementations, alterations, and permutations of the described implementations are within the scope of the following claims as will be apparent to those skilled in the art. For example, the actions recited in the claims can be performed in a different order and still achieve desirable results.

Accordingly, the above description of example implementations does not define or constrain this disclosure. Other changes, substitutions, and alterations are also possible without departing from the spirit and scope of this disclosure.

The invention claimed is:

1. A computer-assisted method, comprising:
receiving, by a computer system, a set of data entries for a drug from a pharmaceutical manufacturer;
receiving, by the computer system, a first prescription data submission from a first specialty pharmacy, wherein:
the first specialty pharmacy and the pharmaceutical manufacturer are not communicatively linked,
the first prescription data submission corresponds to a first prescription for the drug presented to the first specialty pharmacy, and
the first prescription data submission encodes a first set of de-identified fields associated with the first prescription and a medical record;
generating, by the computer system, a first set of report data entries based on the first prescription data submission, wherein the first set of report data entries are anonymized with respect to a patient that presents the first prescription to the first specialty pharmacy;
receiving, by the computer system, a second prescription data submission from a second specialty pharmacy, wherein:
the pharmaceutical manufacturer and the second specialty pharmacy are not communicatively linked,
the second prescription data submission corresponds to a second prescription for the drug presented to the second specialty pharmacy, and
the second prescription data submission encodes a second set of de-identified fields associated with the second prescription and the medical record;
generating, by the computer system, a second set of report data entries based on the second prescription data submission, wherein the second set of report data entries are anonymized with respect to a patient that presents the first prescription to the first specialty pharmacy;
determining, by the computer system, a set of links between the first set of report data entries and the second set of report data entries based on the first set of de-identified fields and the second set of de-identified fields being associated with the same medical record;
determining, by the computer system, a cumulative dose of the drug received by the patient of the medical record is within a safety limit associated with the drug based on the set of links;
providing, by the computer system and to the pharmaceutical manufacturer, an indication that shows the cumulative dose of the drug received by the patient of the medical record is within the safety limit;
receiving, by the computer system and from the pharmaceutical manufacturer, an authorization that permits the second specialty pharmacy to dispense the drug to the patient of the medical record based on the cumulative dose of the drug being within the safety limit; and
providing, by the computer system, an instruction to the second specialty pharmacy to dispense the drug.

2. The method of claim 1, wherein:
the first specialty pharmacy is authorized by a first healthcare insurance carrier to distribute the drug,
the second specialty pharmacy is authorized by a second healthcare insurance carrier to distribute the drug, and
the second healthcare insurance carrier is different from the first healthcare insurance carrier.

3. The method of claim 1, further comprising:
receiving, by the computer system, a second set of data entries for a second drug from a second pharmaceutical manufacturer.

4. The method of claim 3, further comprising:
receiving, by the computer system, a third prescription data submission from the first specialty pharmacy, wherein:
the third prescription data submission corresponds to a third prescription for a second drug presented to the first specialty pharmacy, and
the third prescription data submission encodes a third set of de-identified fields associated with the third prescription and the medical record;
generating, by the computer system, a third set of report data entries based on the third prescription data submission, wherein the third set of report data entries are anonymized with respect to a patient that presents the third prescription to the first specialty pharmacy.

5. The method of claim 4, further comprising:
determining, by the computer system, that the first set of report data entries and the third set of report data entries are associated with the same medical record;
determining, by the computer system, a second set of links between the first set of report data entries and the third set of report data entries based on the first set of de-identified fields and the third set of de-identified fields being associated with the same medical record; and
adjusting, by the computer system, the cumulative dose of the drug based on the second set of links.

6. The method of claim 3, wherein the second pharmaceutical manufacturer is different from the pharmaceutical manufacturer.

7. The method of claim 3, wherein the second pharmaceutical manufacturer is identical to the first pharmaceutical manufacturer.

8. The method of claim 1, wherein receiving the first prescription data submission comprises receiving a request originally from the patient that presents the first prescription to the first specialty pharmacy to participate in a patient-assistance-program (PAP) offered by the first pharmaceutical manufacturer.

9. The method of claim 8, wherein generating first set of report data entries comprises generating a participation request to participate in the PAP offered by the first pharmaceutical manufacturer, the participation request comprising de-identified income characteristics of the patient that presents the first prescription to the first specialty pharmacy.

10. The method of claim 9, wherein the first set of report data entries includes the participation request.

11. The method of claim 10, wherein the authorization received from the pharmaceutical manufacturer comprises a determination result from the pharmaceutical manufacturer indicating the patient that presents the first prescription to the first specialty pharmacy is allowed to participate in the PAP.

12. The method of claim 11, further comprising:
in response to receiving the authorization that includes the determination result indicating the patient that presents the first prescription to the first specialty pharmacy is allowed to participate in the PAP, providing, by the computer system and to a healthcare insurance carrier of the patient that presents the first prescription to the first specialty pharmacy, an indication of the determination result.

13. The method of claim 9, wherein generating the participation request further comprises querying a government agency to confirm the income characteristics of the patient that presents the first prescription to the first specialty pharmacy.

14. The method of claim 1, further comprising:
forwarding, by the computer system, at least a portion of the first set of report data entries to a regulatory agency.

15. The method of claim 14, wherein forwarding at least a portion of the first set of report data entries comprises forwarding at least a portion of the first set of report data entries to comply with a risk mitigation strategy in consuming the drug.

16. A computer system, comprising one or more processors, configured to perform operations of:
receiving, by a computer system, a set of data entries for a drug from a pharmaceutical manufacturer;
receiving, by the computer system, a first prescription data submission from a first specialty pharmacy, wherein:
the first specialty pharmacy and the pharmaceutical manufacturer are not communicatively linked,
the first prescription data submission corresponds to a first prescription for the drug presented to the first specialty pharmacy, and
the first prescription data submission encodes a first set of de-identified fields associated with the first prescription and a medical record;
generating, by the computer system, a first set of report data entries based on the first prescription data submission, wherein the first set of report data entries are anonymized with respect to a patient that presents the first prescription to the first specialty pharmacy;
receiving, by the computer system, a second prescription data submission from a second specialty pharmacy, wherein:
the pharmaceutical manufacturer and the second specialty pharmacy are not communicatively linked,
the second prescription data submission corresponds to a second prescription for the drug presented to the second specialty pharmacy, and
the second prescription data submission encodes a second set of de-identified fields associated with the second prescription and the medical record;
generating, by the computer system, a second set of report data entries based on the second prescription data submission, wherein the second set of report data entries are anonymized with respect to a patient that presents the first prescription to the first specialty pharmacy;
determining, by the computer system, a set of links between the first set of report data entries and the second set of report data entries based on the first set of de-identified fields and the second set of de-identified fields being associated with the same medical record;
determining, by the computer system, a cumulative dose of the drug received by the patient of the medical record is within a safety limit associated with the drug based on the set of links;
providing, by the computer system and to the pharmaceutical manufacturer, an indication that shows the cumulative dose of the drug received by the patient of the medical record is within the safety limit;
receiving, by the computer system and from the pharmaceutical manufacturer, an authorization that permits the second specialty pharmacy to dispense the drug to the patient of the medical record based on the cumulative dose of the drug being within the safety limit; and providing, by the computer system, an instruction to the second specialty pharmacy to dispense the drug.

17. A computer-readable medium, comprising software instructions, that when executed by a computer, cause the computer to execute operations of:

receiving, by a computer system, a set of data entries for a drug from a pharmaceutical manufacturer;

receiving, by the computer system, a first prescription data submission from a first specialty pharmacy, wherein:
the first specialty pharmacy and the pharmaceutical manufacturer are not communicatively linked,
the first prescription data submission corresponds to a first prescription for the drug presented to the first specialty pharmacy, and
the first prescription data submission encodes a first set of de-identified fields associated with the first prescription and a medical record;

generating, by the computer system, a first set of report data entries based on the first prescription data submission, wherein the first set of report data entries are anonymized with respect to a patient that presents the first prescription to the first specialty pharmacy;

receiving, by the computer system, a second prescription data submission from a second specialty pharmacy, wherein:
the pharmaceutical manufacturer and the second specialty pharmacy are not communicatively linked,
the second prescription data submission corresponds to a second prescription for the drug presented to the second specialty pharmacy, and
the second prescription data submission encodes a second set of de-identified fields associated with the second prescription and the medical record;

generating, by the computer system, a second set of report data entries based on the second prescription data submission, wherein the second set of report data entries are anonymized with respect to a patient that presents the first prescription to the first specialty pharmacy;

determining, by the computer system, a set of links between the first set of report data entries and the second set of report data entries based on the first set of de-identified fields and the second set of de-identified fields being associated with the same medical record;

determining, by the computer system, a cumulative dose of the drug received by the patient of the medical record is within a safety limit associated with the drug based on the set of links;

providing, by the computer system and to the pharmaceutical manufacturer, an indication that shows the cumulative dose of the drug received by the patient of the medical record is within the safety limit;

receiving, by the computer system and from the pharmaceutical manufacturer, an authorization that permits the second specialty pharmacy to dispense the drug to the patient of the medical record based on the cumulative dose of the drug being within the safety limit; and providing, by the computer system, an instruction to the second specialty pharmacy to dispense the drug.

* * * * *